US00PP30752P3

(12) United States Plant Patent
Olesen

(10) Patent No.: US PP30,752 P3
(45) Date of Patent: Jul. 30, 2019

(54) COMPACT FLORIBUNDA ROSE PLANT NAMED 'POULPAL077'

(50) Latin Name: ***Rosa* hybrid**
Varietal Denomination: Poulpal077

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/731,974

(22) Filed: Sep. 5, 2017

(65) Prior Publication Data

US 2019/0075700 P1 Mar. 7, 2019

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
See application file for complete search history.

(56) References Cited

PUBLICATIONS

UPOV hit on floribunda rose plant named 'Poulpal077', QZ PBR 48863, filed Sep. 19, 2016.*

* cited by examiner

*Primary Examiner* — Anne Marie Grunberg

(57) ABSTRACT

A new garden rose plant of the Compact Floribunda class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal077'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal077', originated as a single seedling from the stated cross.

The new variety may be distinguished from its male pollen parent and female seed parent primarily by the following characteristics. The male pollen parent plant has small diameter flowers, about 50 mm, while the new variety has flower diameter of 95 mm. The female seed parent plant has light pink flowers, flowers while the new variety has deep pink flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance.

This combination of qualities is not present in previously available commercial cultivars of this type, known to the inventor, and distinguish 'Poulpal077' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal077' was selected in the spring of 2012 by the inventor as a single plant from the progeny of the aforementioned hybridization.

Asexual reproduction of 'Poulpal077' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal077' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal077'.

Specifically illustrated in FIG. 1 of the drawings are open flowers, petals detached, sepals detached, receptacle, and reproductive flower parts.

Figure 1:
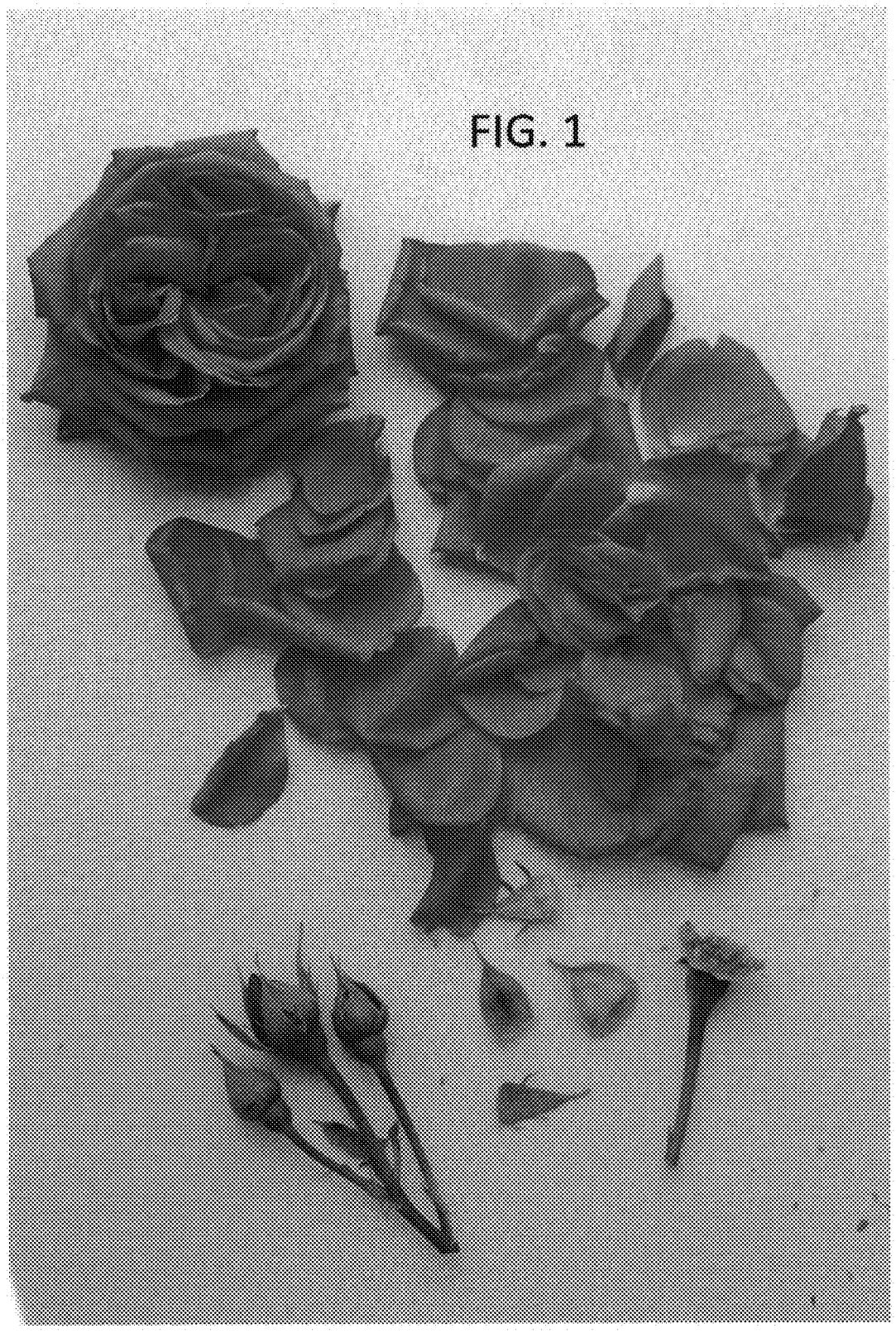
Figure 2:
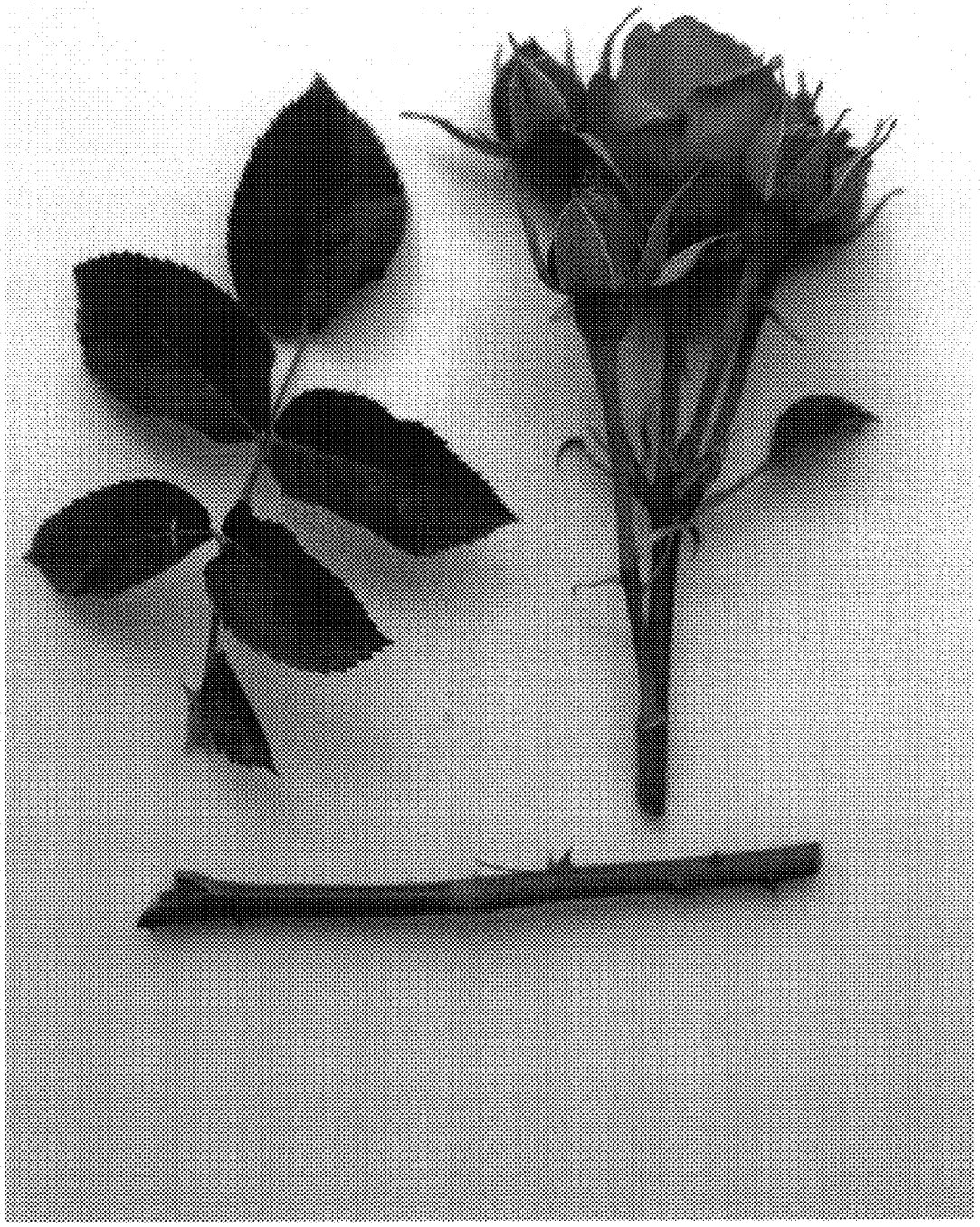

Illustrated in FIG. 2 of the drawings are a cluster of flowers on a branch, a mature leaf, and bare stem showing prickles. Plants shown are 2 years of age.

DETAILED DESCRIPTION OF THE VARIETY

The following is a description of 'Poulpal077', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas031', U.S. Plant Pat. No. 22,502 are compared to 'Poulpal077' in Chart 1.

CHART 1

| | 'Poulpal077' | 'Poulcas031' |
|---|---|---|
| Petal Count | 60 | 40 to 50 |
| Flower Diameter | 95 mm | 70 to 80 mm |
| General Tonality of Flower Color | Red-Purple Group 61C | Red-Purple Group N 57A |

FLOWER AND FLOWER BUD

Blooming habit: Continuous.

Flower bud:

*Size.*—Upon opening, 27 mm in length from base of receptacle to end of bud. Bud diameter is 19 mm.

*Bud form.*—Ovoid.

*Bud color.*—As sepals divide petals are Greyed-Purple Group 60A.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—25 mm long, 18 mm wide.

*Receptacle.*—Texture: Smooth. Size: 11 mm in height, 11 mm wide. Color: Yellow-Green Group 144A. Shape: Campanulate.

*Pedicel.*—Surface: Smooth. Length: 40 to 45 mm. Diameter: 2 mm on average. Color: Yellow-Green Group N144A with intonations of Greyed-Red Group 179A. Strength: Strong.

*Peduncle.*—Length: 2 to 4 cm. Diameter: About 4 mm. Color: Yellow-Green Group N144A with intonations of Greyed-Red Group 179A. Texture: Smooth.

Flower bud development: Flower buds are borne in clusters of about 5 flower buds per stem.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 95 mm when open. Flower depth is 50 mm.

*Flower shape.*—Quartered-rosette, very double, with many overlapping petals packed into quarter sections.

*Shape of flower, side view.*—The upper portion is flat. The lower portion is a flattened convex.

Petalage: Under normal conditions, flowers have about 60 petals.

General tonality of flower: Open flowers are Red-Purple Group 61C.

Petal color:

*Upon opening, outer petals.*—Upper surface: Red-Purple Group 61C. Lower surface: Red-Purple Group 61B.

*Upon opening, inner petals.*—Upper surface: Red-Purple Group 61C. Lower surface: Red-Purple Group 61B.

*Basal petal spots, upon opening.*—Upper surface: Yellow Group 6B. Lower surface: Yellow Group 4B.

*After opening, inner and outer petals.*—Upper surface: Red-Purple Group 68A with intonations of Red-Purple Group 68C. Lower surface: Red-Purple Group 61C with intonations of Red-Purple Group 61D.

*Basal petal spots, after opening.*—Upper surface: Yellow Group 6D. Lower surface: Yellow Group 4D.

Petals:

*Petal reflex.*—Outer petals are strongly reflexed.

*Margin.*—Moderate to strong undulation, with occasional clefts at the apex.

*Shape.*—Broad and elliptic. Apex shape: Rounded. Base shape: Acute.

*Size.*—50 mm (l)×60 mm (w).

*Texture.*—Smooth.

*Thickness.*—Average.

Reproductive flower parts:

*Pollen.*—None observed.

*Anthers.*—Size: 2 mm in length. Color: Yellow Group 7A. Quantity: 60 on average.

*Filaments.*—Color: Yellow Group 13B. Length: 4 mm.

*Pistils.*—Length: 5 mm. Quantity: 40 on average.

*Stigmas.*—Color: Yellow Group 4A.

*Styles.*—Color: Orange-Red Group 32D.

*Location of stigmas.*—Level in location relative to the length of the filaments and the height of the anthers.

*Hips.*—None Observed.

PLANT

Plant growth: Upright, bushy. Plants are 60 cm in height, and 55 cm wide.

Stems:

*Color of juvenile growth.*—Yellow-Green Group 144B.

*Color of mature growth.*—Yellow-Green Group 144A.

*Length.*—Canes are about 30 cm from the base of the plant to the flowering portion.

*Diameter.*—About 8 mm.

*Internodes.*—On mature canes about 30 mm between nodes.

*Surface texture.*—Young wood: Smooth. Older wood: Smooth.

Long prickles:

*Incidence.*—5 prickles per 10 cm of stem.

*Size.*—Average length of prickles on mature stems is 7 mm.

*Shape.*—Upper portion is linear. Lower portion is concave.

*Color.*—Juvenile prickles: Greyed-Orange Group 173B. Mature prickles: Greyed-Orange Group 173B.

Plant foliage:

*Compound leaf.*—150 mm (l)×110 (w).

*Quantity.*—2 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage*.—Upper side: Yellow-Green Group 146A. Lower side: Yellow-Green Group 146B.

Plant leaves and leaflets:

*Stipules*.—Size: 20 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 35 mm. Diameter: 2 mm. Upper surface color: Yellow-Green Group 144A. Lower surface color: Yellow-Green Group 144A.

*Rachis*.—Length: 50 mm. Upper surface color: Yellow-Green Group 144A. Lower surface color: Yellow-Green Group 144A.

*Leaflet*.—Quantity: Normally 5 to 7 leaflets. Margins: Serrated. Size: Terminal leaflets are about 60 mm long, 41 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal077', substantially as illustrated and described herein, due to its abundant pink flowers, disease resistance, and extended period of bloom.

* * * * *